United States Patent [19]
Govindan

[11] Patent Number: 5,053,531
[45] Date of Patent: Oct. 1, 1991

[54] QUATERNARY AMMONIUM ANTISTATIC COMPOUNDS

[75] Inventor: Cheruthur Govindan, Wadsworth, Ohio

[73] Assignee: PPG Industries, Inc., Pittsburgh, Pa.

[21] Appl. No.: 449,651

[22] Filed: Dec. 12, 1989

Related U.S. Application Data

[62] Division of Ser. No. 268,903, Nov. 8, 1988, Pat. No. 4,904,825.

[51] Int. Cl.$^5$ ............................................. C07C 213/00
[52] U.S. Cl. .................................... 562/114; 564/292; 564/291
[58] Field of Search ................... 562/84, 114, 84; 544/170, 177; 260/501.15; 564/287, 291, 292

[56] References Cited

U.S. PATENT DOCUMENTS

| | | | |
|---|---|---|---|
| 2,897,170 | 7/1959 | Gruber | 260/326 |
| 3,113,956 | 12/1963 | Robinette, Jr. | 260/459 |
| 3,117,113 | 1/1964 | Tudor | 360/97.8 |
| 3,383,410 | 5/1968 | Johnson et al. | 260/501.21 |
| 3,398,097 | 8/1968 | Kersnar et al. | 250/152 |
| 3,661,945 | 5/1972 | Mannheimer | 260/401 |
| 3,699,066 | 10/1972 | Hunsucker | 260/22 EP |
| 3,914,496 | 10/1975 | Jorek et al. | 428/279 |
| 3,933,697 | 1/1976 | Fujii et al. | 260/2.5 A |
| 3,933,779 | 1/1976 | Baron et al. | 260/93.5 |
| 3,972,855 | 8/1976 | Martinsson et al. | 260/567.6 M |
| 3,974,076 | 8/1976 | Wiersema et al. | 252/8 |
| 4,070,531 | 1/1978 | Schwarzl et al. | 526/6 |
| 4,118,525 | 10/1978 | Jones | 427/242 |
| 4,144,367 | 3/1979 | Landucci | 428/96 |
| 4,171,323 | 10/1979 | Marin et al. | 260/501.19 |
| 4,189,550 | 2/1980 | Schwarze et al. | 525/6 |
| 4,259,373 | 3/1981 | Demessemaekers | 427/242 |
| 4,476,045 | 10/1984 | O'Lenick | 252/545 |
| 4,540,521 | 9/1985 | Garst et al. | 260/459 A |
| 4,552,687 | 11/1985 | Beacham et al. | 252/500 |
| 4,675,180 | 5/1987 | Gunter | 424/70 |
| 4,711,776 | 12/1987 | Suzuki et al. | 424/70 |
| 4,752,527 | 6/1988 | Sanzero et al. | 428/391 |
| 4,828,765 | 5/1989 | Ohlendorf et al. | 260/501.15 |

FOREIGN PATENT DOCUMENTS

| | | |
|---|---|---|
| 12215A2 | 6/1980 | European Pat. Off. |
| 2849065 | 6/1979 | Fed. Rep. of Germany |
| 902587 | 8/1962 | United Kingdom |
| 1014539 | 12/1965 | United Kingdom |

Primary Examiner—Joseph L. Schofer
Assistant Examiner—Jeffrey T. Smith
Attorney, Agent, or Firm—Irwin M. Stein

[57] ABSTRACT

Described are certain quaternary ammonium alkyl benzene sulfonate salts and certain quaternary ammonium alkane sulfonate salts, e.g., octyl dimethyl hydroxyethyl ammonium dodecyl benzene sulfonate and octyl dimethyl hydroxyethyl ammonium methane sulfonate which are useful as antistatic agents for synthetic polymer articles.

6 Claims, No Drawings

QUATERNARY AMMONIUM ANTISTATIC COMPOUNDS

This is a division of application Ser. No. 07/268,903, filed Nov. 8, 1988, now U.S. Pat. No. 4,904,825.

DESCRIPTION OF THE INVENTION

The present invention relates to certain novel quaternary ammonium sulfonate compounds and, more particularly, relates to the use of such compounds as internal and external antistatic agents for normally non-conducting organic materials. Still more particularly, the present invention relates to shaped articles of synthetic and naturally ocurring organic polymers that have less than their normal tendency to accumulate static charges of electricity.

Organic polymers, e.g., synthetic polymers, are essentially electrical insulators, i.e., non-conductors of electricity. Articles prepared from such polymers tend to develop electrostatic charges upon their surfaces when they are in a dry state and are subjected to friction during their production and finishing or during their handling and use. Such static charges are undesirable for a number of reasons. For example, surface static charges readily attract dust and other contaminants, which are unsightly and difficult to clean. Often the contaminants or static charges themselves cause processing or handling problems. In certain cases, static charges may accumulate to a level where an unpleasant electric shock is experienced when the article is handled. Further, a high level of static charge on a molded part covering sensitive electronic equipment can damage such equipment.

Articles prepared from non-conducting polymers may be surface treated with a finish containing an antistatic agent; however, surface treatments are less desirable than internally incorporated antistatic agents due to a wearing away of the applied finish. Conversely, antistatic agents that are incorporated within the shaped article by, for example, blending the antistatic agent with the synthetic polymer prior to forming of the article, are susceptible to decomposition as a result of the high temperatures used to form the article, e.g., by molding and extrusion. There is, therefore, a continuing need for more thermally stable antistatic agents that may be used with synthetic and naturally occurring polymers, and other naturally occurring materials.

The art has described the use of certain quaternary ammonium p-toluene sulfonate salts as antistatic agents. While some of these salts are relatively thermally stable, e.g., at temperatures of about 200° C., their performance as antistatic agents is not as efficacious as desired. In particular, the decay time of a charge applied to an article treated with the antistatic agent is too long. It is preferred that such decay times be less than 2 seconds, more preferably less than 1 second, and still more preferably less that 0.6 seconds.

It is an object of the present invention to provide novel antistatic agents for use internally or externally with formed synthetic materials, e.g., polymers, and other articles of manufacture to lessen the accumulation thereon of surface static charges.

It has now been discovered that certain quaternary ammonium sulfonate salts possess both thermal stability and markedly improved antistatic properties, i.e., electrostatic buildup and dissipation properties. Such properties may be measured by Federal Test Standard 101C, Method 4046, which measures the decay time for an applied charge of 5,000 volts. More particularly, the aforesaid quaternary salts may be represented by the following graphic formula I:

wherein

R is a $C_2$-$C_{22}$ alkyl, preferably a $C_8$-$C_{18}$ alkyl, and $R_1$ is selected from the group consisting of $C_1$-$C_{22}$ alkyl and an alkyleneoxy radical, "Z", that may be represented by the formula, $-CH_2-C(A)H-O]_xH$, wherein A is hydrogen, methyl or ethyl, and x is an integer of from 1-5, e.g., hydroxyethyl, hydroxypropyl, hydroxybutyl, poly(ethyleneoxy) hydroxyethyl, poly(propyleneoxy) 2-hydroxypropyl, and poly(butyleneoxy)2-hydroxybutyl. Preferably, $R_1$ is selected from the group consisting of $C_1$-$C_3$ alkyl or $C_8$-$C_{18}$ alkyl, e.g. methyl, ethyl, n-propyl, isopropyl, octyl, decyl, dodecyl, hexadecyl, and octadecyl, or the alkyleneoxy radical Z wherein A is hydrogen or methyl and x is 1 to 3. Still more preferably, $R_1$ is a $C_1$-$C_3$ alkyl or alkyleneoxy radical Z wherein A is hydrogen and x is 1 to 2. When x is greater than 1, the sulfonate compound may be liquid, which makes it easier to handle.

$R_2$ in the above graphic formula I is selected from the group consisting of $C_1$-$C_3$ alkyl, e.g., methyl, ethyl, n-propyl and isopropyl and the radical Z, wherein A and x are as defined with respect to $R_1$. Alternatively $R_1$ and $R_2$ may also join together to form a six-membered morpholino group.

$R_3$ in the above graphic formula I is a group represented by the alkyleneoxy radical Z, wherein A and x are as defined with respect to $R_1$; and Y is the anion, $R'SO_3$, wherein R' is a $C_1$-$C_{18}$ alkyl, preferably a $C_1$-$C_2$ alkyl, e.g., methyl and ethyl, or a $C_8$-$C_{18}$ alkylphenyl, preferably a $C_{10}$-$C_{13}$ alkylphenyl. Preferably, the alkyl phenyl is a para-alkylphenyl.

With respect to R, $R_1$, and R', the term alkyl denotes a univalent, essentially saturated branched or straight chained alkyl group. Representative of such alkyl groups include methyl, ethyl, propyl, butyl, pentyl, hexyl, isohexyl, heptyl, octyl, nonyl, decyl, undecyl, dodecyl, cocoyl, tridecyl, tetradecyl, pentadecyl, hexadecyl, heptadecyl, octadecyl, soya, eicosyl and the like. When derived from naturally occurring materials, the group R, $R_1$, and R' may contain a small amount of unsaturation and may be comprised of a mixture of alkyl groups. For example, commercially available dodecyl benzene sulfonic acid is a benzene sulfonic acid in which the alkyl substituent on the benzene ring is a mixture of $C_{10}$-$C_{13}$ alkyl groups, the nominal number of carbon atoms being about 12.

The aforedescribed quaternary ammonium sulfonate salts may be more graphically illustrated by the following graphic formulae II and III where R, $R_1$, $R_2$, and $R_3$ have the meanings described heretofore with respect to graphic formula I, $R_a$ is a $C_1$-$C_{18}$ alkyl, e.g., $C_1$-$C_2$ alkyl, and $R_b$ is a $C_8$-$C_{18}$ alkyl, preferably a $C_{10}$-$C_{13}$ alkyl. As shown, $R_b$ is a para-alkyl substituent, but it may be an ortho- or meta-substituent.

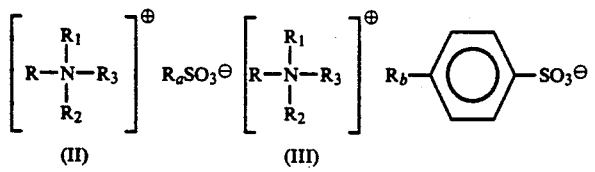

(II)   (III)

Non-limiting examples of quaternary ammonium sulfonate compounds illustrated by graphic formula I include both the alkane sulfonate salts, such as methane sulfonate salts, and the alkyl benzene sulfonate salts, such as p-alkyl benzene sulfonate salts, that are described in Table I. There, R, $R_1$, $R_2$, $R_3$ and $R_b$ are selected from the substituents tabulated therein.

TABLE 1

| A. Methane Sulfonates | | | | |
|---|---|---|---|---|
| | | SUBSTITUENT | | |
| Compound/ | R | $R_1$ | $R_2$ | $R_3$ |
| 1 | Octyl | Methyl | Methyl | Hydroxyethyl |
| 2 | Octyl | Ethyl | Ethyl | Hydroxyethyl |
| 3 | Soya | Methyl | Methyl | Hydroxyethyl |
| 4 | Decyl | Decyl | Methyl | Hydroxyethyl |
| 5 | Octyl | Methyl | Methyl | 2-hydroxypropyl |
| 6 | Octyl | Methyl | Methyl | 3-hydroxybutyl |
| 7 | Octyl | 4-Morpholino | | Hydroxyethyl |
| 8 | Octyl | Methyl | Hydroxyethyl | Hydroxyethyl |
| 9 | Decyl | Hydroxyethyl | Hydroxyethyl | Hydroxyethyl |
| 10 | Octyl | Hydroxyethyl | Hydroxyethyl | Hydroxyethyl |
| 11 | Octyl | Methyl | Methyl | Poly(ethyleneoxy) hydroxyethyl |
| 12 | Cocoyl | Hydroxyethyl | Hydroxyethyl | Hydroxyethyl |

| B. p-Alkyl Benzene Sulfonates | | | | | |
|---|---|---|---|---|---|
| Compound/ | R | $R_1$ | $R_2$ | $R_3$ | $R_b$ |
| 1 | Octyl | Methyl | Methyl | Hydroxyethyl | Dodecyl |
| 2 | Octyl | Methyl | Methyl | 2-hydroxypropyl | Dodecyl |
| 3 | Octyl | Methyl | Methyl | 3-hydroxybutyl | Dodecyl |
| 4 | Soya | Methyl | Methyl | Hydroxyethyl | Dodecyl |
| 5 | Octyl | Octyl | Methyl | Hydroxyethyl | Dodecyl |
| 6 | Decyl | Decyl | Methyl | Hydroxyethyl | Dodecyl |
| 7 | Octyl | Methyl | Methyl | Poly(ethyleneoxy) hydroxyethyl | Dodecyl |

Compound 1 in Table 1, Part A may be named octyl dimethyl 2-hydroxyethyl ammonium methane sulfonate (where Y is methane sulfonate). Compound 1 in Table 1, Part B may be named octyl dimethyl 2212 -hydroxyethyl ammonium p-dodecyl benzene sulfonate (where Y is dodecyl benzene sulfonate). Other sulfonate salts of the compounds from Table 1 may be similarily named by utilizing the appropriate IUPAC radical name for the designated substituents.

The quaternary ammonium sulfonate salts of graphic formula I may be used to minimize the accumulation of static electricity on non-conducting articles, e.g., articles prepared from synthetic polymers, by applying to the surface of or incorporating within the article effective antistatic amounts of at least one of the salts. Generally, the compounds of graphic formula I may be incorporated within the article in amounts of between about 0.5 and about 20 weight percent and preferably are used in amounts of between about 2 and about 6 weight percent, based on the weight of the dry, untreated article. When associated with a finish composition, the compounds of graphic formula I are generally present in amounts of from about 0.1 to about 2, e.g., 0.5 to 1, weight percent.

When compounded into a shaped article of a synthetic polymer, the antistatic quaternary ammonium sulfonate salt will migrate or "bloom" to the surface of the article to provide an antistatic coating thereon. Such a coating is more permanent than an externally (topically) applied coating since the latter can be removed by wear, wiping, washing, handling, movement in transit, etc. In contrast, if the migrated layer of an internally compounded antistatic agent should be removed during handling or processing, a new antistatic layer will bloom to the surface.

To apply the antistatic compound topically to the surface of an article, the antistatic compound is dissolved or dispersed in water, lower alkanol, e.g., a $C_1$-$C_4$ alcohol, lubricating oil, polymeric coating, other organic solvent, etc. and the resulting "finish" containing the desired amount of antistatic compound applied to the surface using conventional coating techniques, e.g., spraying, dipping, wiping, etc., thereby to deposit an effective amount of antistatic agent on the surface of the article.

In general, the antistatic compounds of graphic formula I are thermally stable at temperatures in excess of 200° C. When heated to temperatures up to about 275° C., weight losses of less than 5 weight percent have been observed for compounds such as octyl dimethyl hydroxyethyl ammonium methane sulfonate. The compounds may be solids, liquids or low melting waxes, depending on the number of carbons in the R, $R_1$, $R_a$ and $R_b$ alkyl groups. At the same time, these compounds are more antistatic, i.e., exhibit shorter decay times, than sulfonate salts currently in commercial use, e.g., p-toluene sulfonate salts.

When antistatic compounds are incorporated internally into an article, the compound may be mixed in antistatic amounts with the synthetic polymer or other material by conventional blending or mixing equipment, e.g., Banbury mixers or other rubber and plastic processing equipment, and the mixture formed into the article, e.g., by extrusion or other molding procedure. Alternatively, a master batch of the polymer and antistatic compound may be prepared and the master batch added in antistatic amounts to synthetic polymer that is to be formed into an article, thereby to provide the desired antistatic amount of antistatic compound within the article. A master batch may contain between about 10 and about 25 percent by weight of the antistatic compound.

The compounds of graphic formula I may be used with conventional synthetic polymers utilized to prepare formed articles. The compatibility of the antistatic compounds with a particular synthetic polymer may be readily determined by those skilled in the art. Antistatic compounds of graphic formula I may be used in a wide spectrum of substrate shapes, such as fibers (woven and nonwoven), sheets, films and molded or extruded articles. Such articles may be prepared from thermoplastic or thermosetting polymers or copolymers (including terpolymers).

Non-limiting examples of synthetic polymers from which formed articles may be prepared include polyolefins, such as polyethylene, polypropylene and polyisobutylene, styrene resins such as polystyrene, poly(chlorostyrene), styrene-acrylonitrile copolymers, poly(styrene-acrylonitrile-butadiene) terpolymers (ABS resins) and high impact polystyrene (HIPS), polyesters such as poly(methylacrylate), poly(methylmethacrylate) and poly(vinylacetate), ethylene glycolterephthalic acid polymers, polycarbonates, polyamides such as nylon and Kevlar ® type polyamides, polyacetals such as poly(vinylbutyral), phenol-formaldehyde resins, vinyl resins, such as poly(vinyl chloride), poly(vinylidene chloride), polytrifluorochloroethylene, copolymers of vinyl chloride with vinyl acetate, vinylidene chloride, or acrylonitrile, polyurethanes, and poly(phenylene ether) resins. Mixtures of the aforesaid polymers may also be used, e.g., polymer alloys.

In addition, the compounds of graphic formula I may be used with natural materials or mixtures of natural and synthetic materials, e.g., rayon, acetate, rayon-cellulosic materials such as cellulose acetate-propionate, cellulose-butyrate, cotton, linen, jute, ramie, wool, mohair and glass, e.g., fiberglass and fiberglass insulation. The textile materials may take any form, including individual fibers, woven material such as fabrics, cloth, carpets, rugs and upholstery and non-woven materials such as felts, bats and mats. In the case of fiberglass strand or fiberglass insulation, the compounds of graphic formula I may be applied topically as a finish or as part of a sizing composition.

The compounds of graphic formula I may be prepared by reacting approximately equal molar amounts of the tertiary amine and an ester of alkane sulfonic acid or alkyl benzene sulfonic acid in the presence of a solvent, e.g., water, lower alkanols, e.g., $C_1-C_4$ alkanols, or acetone, at tempatures of from about 25° C. to about 250° C., e.g., from about 65° to 80° C., under a slight positive nitrogen pressure. Preferably, the compounds of graphic formula I may be prepared more readily by reacting the corresponding tertiary amine, corresponding sulfonic acid, e.g., methane sulfonic acid, and alkylene oxide, e.g., ethylene oxide, in accordance with the following equation IV.

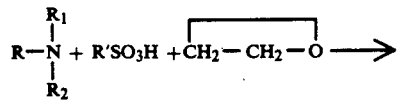    IV

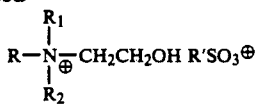

Quaternization of tertiary amines with alkylene oxide is preferably performed in the presence of a small amount of amine catalyst and at elevated pressures, the later accelerating the take-up of the alkylene oxide. Quaternary amines containing poly(alkylene oxide), e.g., poly(ethylene oxide) groups may preferably be prepared in the presence of a slight excess of the amine, an excess of alkylene oxide and at elevated pressures, which may be from about 10 to about 100 pounds per square inch (0.07–0.7 MPa).

The present invention is more particularly described in the following examples which are intended as illustrative only since numerous modifications and variations will be apparent to those skilled in the art.

EXAMPLE 1

118.0 grams (0.75 moles) of n-octyl dimethylamine were neutralized with a solution of 72.0 grams (0.75 moles) of methane sulfonic acid in 100 milliliters of water. The temperature of the resulting mixture rose to about 80°–90° C. and thereafter was cooled to about 40° C. The reaction mixture was charged to an autoclave and, after thoroughly flushing the system with nitrogen, the autoclave was sealed and pressurized with nitrogen to 20 pounds per square inch (psig) (0.1 MPa). The contents of the autoclave were heated to about 70° C. and 62.0 grams (1.4 moles) of ethylene oxide charged to the autoclave. The contents of the autoclave were stirred for 1 hour while maintaining the temperature at 70° C. Thereafter, the autoclave was flushed with nitrogen and the reaction mixture cooled. The pH of the cooled solution in the autoclave was determined to be about 10.5 and subsequently adjusted to about 4.7 using methane sulfonic acid and a 50 percent sodium hydroxide aqueous solution. 50.0 grams of the solution in the autoclave were stripped under vacuum; the residue dissolved in an acetone-ether solution; and the solution decolorized with charcoal. The decolorized mixture was filtered and concentrated to obtain 31.5 grams of a clear liquid that solidified on standing. The product, n-octyl dimethyl hydroxyethyl ammonium methane sulfonate, was confirmed by discharge ionization secondary ion mass spectrometry (DISIMS).

EXAMPLE 2

62.0 grams (0.28 moles) of n-octyl diethanol amine were neutralized with a solution of 27.0 grams (0.28 moles) of methane sulfonic acid in 100 milliliters of water. The pH of the mixture was determined to be about 5.3 and was adjusted subsequently to 6.3 with octyl dimethyl amine. 50 milliliters of water were added to the neutralized mixture and the resulting solution charged to an autoclave, which was first flushed with nitrogen and then pressurized with nitrogen to 20 psig (0.1 MPa). The contents of the autoclave were heated to 65° C. and 25.0 grams (0.37 moles) of ethylene oxide added thereto over a period of 30 minutes. After addition of the ethylene oxide, the nitrogen pressure was increased to 100 pounds psig (0.7 MPa) and the reaction mixture stirred for 2 hours. The reaction mixture was then cooled, the autoclave flushed with nitrogen, and the contents of the autoclave stripped under vacuum to obtain 108 grams of a viscous liquid. The product, n-octyl tris(hydroxyethyl) ammonium methane sulfonate, was confirmed by DISIMS spectrometry.

EXAMPLE 3

To a solution of 123.3 grams (0.41 moles) of soya dimethyl amine in 200 milliliters of isopropanol were added with stirring 132.0 grams of dodecyl benzene sulfonic acid. The temperature of the mixture rose to about 50° C. The pH of the mixture was determined to be about 1.8. The mixture was charged to an autoclave, which was sealed and pressurized with nitrogren to 20 psig (0.1 MPa). The mixture was heated to 70° C. and 35.0 grams (0.80 moles) of ethylene oxide added to the reactor over a period of 30 minutes. The mixture was stirred overnight while maintaining it at a temperature of 70° C. The pressure was then released and the contents of the autoclave cooled. Isopropanol was stripped from the crude reaction product on a rotary evaporator to obtain 252 grams of a slight yellow paste. The structure of the product was determined by mass spectroscopy to be a mixture corresponding to n-soya dimethyl hydroxyethyl ammonium dodecyl benzene sulfonate.

EXAMPLE 4

To a solution of 160.0 grams (0.5 moles) of dodecyl benzene sulfonic acid in 150 milliliters of ethanol were added with stirring 78.3 grams (0.5 moles) of octyl dimethyl amine. The mixture was charged to an autoclave which was pressurized with nitrogen to a pressure of 20 psig (0.1 MPa.) The mixture was heated to 65° C. and 28.0 grams (0.64 moles) of ethylene oxide added with stirring to the autoclave over a period of 30 minutes. The mixture was then stirred for 2 hours while maintaining it at a temperature of 65° C. The pressure in the autoclave was released, the contents cooled and the ethanol solvent stripped in vacuo to obtain 244.0 grams of a thick liquid.

Since no weight gain was observed, the liquid product was redissolved in 200 milliliters of isopropanol and charged to an autoclave. The contents of the autoclave were warmed to 80° C. and the autoclave pressurized with nitrogen to 20 psig (0.1 MPa). Ethylene oxide (44.0 grams, 1.0 mole) was added to the autoclave over a period of 30 minutes and the autoclave contents stirred overnight while maintaining the contents of the autoclave at a temperature of 80° C. and at a pressure of 100 psig (0.7 MPa). The pressure was released and the reaction product cooled. The isopropanol solvent was stripped in vacuo to obtain 262.0 grams of a light yellow gel. This product was found to be octyl dimethyl hydroxyethyl ammonium dodecyl benzene sulfonate by mass spectroscopy.

EXAMPLE 5

To a solution of 160.0 grams of dodecyl benzene sulfonic acid in 100 milliliters of isopropanol were added 79.5 grams of octyl dimethyl amine. The mixture was charged to an autoclave which was pressurized with nitrogen to a pressure of 20 psig (0.1 MPa). The mixture was warmed to 80° C. and 35.0 grams of propylene oxide added with stirring to the autoclave over a period of about 30 minutes. The mixture was stirred overnight while maintaining it at a temperature of 80° C. In the morning the autoclave pressure had dropped to 10 psig (0.07 MPa), which indicated that the autoclave seal had a leak.

The solvent was stripped from the mixture and the residue (256.8 grams) redissolved in 150 milliliters of isopropanol and the solution charged to the autoclave. Propylene oxide (30.0 grams) was added to the autoclave, the contents warmed to 80° C. and the autoclave pressurized to 30 psig (0.2 MPa) with nitrogen. The pressure dropped to 20 psig (0.1 MPa) in 1 hour. The mixture was stirred overnight at a temperature of 60° C. In the morning the pressure was found to be about 5 psig (0.03 MPa). The mixture was cooled and the solvent stripped on a rotary evaporator. The residue (270.5 grams) was the product octyl dimethyl 2-hydroxypropyl ammonium dodecyl benzene sulfonate, which was confirmed by mass spectroscopy.

EXAMPLE 6 (COMPARATIVE)

157.3 grams of octyl dimethyl amine were charged to an autoclave and neutralized with a solution of 189.5 grams of p-toluene sulfonic acid in 100 milliliters of water. The temperature of the mixture was about 60° C. at the end of the neutralization step. The autoclave was sealed, flushed twice with nitrogen and pressurized to 25 psig (0.2 MPa) with nitrogen. The mixture was warmed to 75°–80° C. and 46.0 grams of ethylene oxide added to the autoclave over about 1 hour. The mixture was stirred at 70° C. for 1 hour.

The pressure in the autoclave was released and the product recovered. A portion of the product was stripped in vacuo and the residue washed with ether. A white powder product was obtained by filtration. Mass spectroscopy confirmed the product to be octyl dimethyl hydroxyethyl ammonium p-toluene sulfonate.

EXAMPLE 7

An aqueous solution containing 0.09 weight percent of the compound of Example 1 was prepared. A 3 ½inch (8.9 cm) ×5 inch (12.7 cm) swatch of an acrylic fabric obtained from Testfabrics Inc. was immersed in 100 grams of the aqueous solution for 30 seconds. Excess solution was squeezed from the swatch using an Atlas laboratory wringer. The swatches were air dried and then conditioned for 24 hours in a controlled humidity chamber maintained at 15 percent relative humidity. This procedure was repeated with the compounds of Examples 2, 4, 5 and 6, and with the commercial antistatic compound Hexcel ®106G. Electrostatic properties of the swatches were measured in accordance with Federal Test Standard 101C, Method 4046 by applying a charge of 5,000 volts to each of the acrylic fabric swatches and measuring the time in seconds required for the charge to decay to 0 volts with an Electrotech Systems static decay meter, Model 406C. Results are tabulated in Table 2.

TABLE 2

| Example (Compound) | 1 | 2 | 4 | 5 | 6 | Hexcel 106G* |
|---|---|---|---|---|---|---|
| Decay Time (sec) | 0.3 | 0.5 | 0.6 | 0.9 | 10 | 1.7 |

*octyl methyl di(hydroxyethyl) ammonium p-toluene sulfonate

The data of table 2 show that compounds of graphic formula I, e.g., compounds of Examples 1,2,4 and 5 have excellent antistatic properties—exhibiting superior decay times compared to the compound of Example 6 (octyl dimethyl hydroxyethyl p-toluene sulfonate) and significantly improved decay times compared to the commercial antistatic product Hexcel ®106G.

EXAMPLE 8

Noryl ® N-190 modified poly(phenylene oxide) resin and 2 weight percent of antistatic compound corresponding to Example 1 were blended for 5 minutes in a Brabender mixer (100 rpm) at 210° C. The resulting mixture was compression molded at 440° F. (227° C.) into a flat plaque about 55 mils thick. The aforesaid procedure was repeated except that 5 weight precent of the antistatic compound was used.

Five inch (12.7 cm) square discs cut from each of the plaques were conditioned for 24 hours in a controlled humidity chamber maintained at 15 percent relative humidity. The surface resistivity and electrostatic property (decay time) of the discs were measured using the test method described in Example 7. Results are tabulated in Table 3.

EXAMPLE 9

The procedure of Example 8 was repeated using the compound of Example 4. Results are tabulated in Table 4.

EXAMPLE 10

High impact polystyrene (HIPS-Mobil polystyrene 4226) and 2 weight percent of antistatic compound corresponding to Example 1 were blended for 3 minutes in a Brabender mixer (100 rpm) at 210° C. The resulting mixture was compression molded at 420° F. (216° C.) into a flat plaque about 55 mils thick. The procedure was repeated except that 5 weight percent of the antistatic compound was used. The surface resistivity and electrostatic property of each of the plaques were tested in the manner described in Example 8. Results are tabulated in Table 3.

EXAMPLE 11

The procedure of Example 10 was repeated using the compound of Example 4. Results are tabulated in Table 4.

EXAMPLE 12

A poly(vinyl chloride) plastisol resin was prepared in the following manner. 92 parts of Geon 173 dispersion resin and 8 parts of Borden 260 ss blending resin were mixed in a blender. 49 parts of dioctyl phthalate and 4 parts of Synpron 1363 thermal stabilizer were mixed and the mixture added with stirring slowly to the blender. After all of the dioctyl phthalate/stabilizer blend had been added, the resulting mixture was stirred for an additional 5 minutes. 0.75 grams of the antistatic compound corresponding to Example 1 was added to 14.25 grams of the plastisol resin and the mixture stirred well. A 10 mil film was drawn down on a 7 inch (17.8 cm) square piece of cardboard and the film cured at 193° C. for 2 minutes. The surface resistivity and electrostatic property of the film were measured using the method described in Example 7. Results are tabulated in Table 3.

EXAMPLE 13

The procedure of Example 12 was repeated using the compound of Example 4. Results are tabulated in Table 4.

TABLE 3

| | PLASTIC RESIN | | | | |
| | NORYL | | HIPS | | PVC PLASTISOL |
| Antistat, Wt % | 2 | 5 | 2 | 5 | 5 |
| --- | --- | --- | --- | --- | --- |
| Decay Time, Secs | 1.2 | 0.2 | 0.9 | 0.03 | 0.07 |
| Resistivity, ohm/sq | $3 \times 10^{10}$ | $5 \times 10^{11}$ | $2 \times 10^{11}$ | $3 \times 10^{9}$ | $1.5 \times 10^{10}$ |

The data of Table 3 shows that the compound of Example 1 exhibits excellent antistatic properties—showing decay times of less than 1 second for each of the plastic resins at the 5 percent level.

TABLE 4

| | PLASTIC RESIN | | | | |
| | NORYL | | HIPS | | PVC PLASTISOL |
| Antistat, Wt % | 2 | 5 | 2 | 5 | 5 |
| --- | --- | --- | --- | --- | --- |
| Decay Time, secs | 1.8 | 0.7 | 3.1 | 1.1 | 0.5 |
| Resistivity, ohm/sq | $8 \times 10^{11}$ | $2 \times 10^{11}$ | $1 \times 10^{12}$ | $4 \times 10^{11}$ | $5 \times 10^{10}$ |

The data of Table 4 show that the compound of Example 4 has good antistatic properties at a 2 weight percent level and very good antistatic properties at a 5 weight percent level—showing decay times of about 1 second or less for the later level of compounding.

EXAMPLE 14

To a solution of 48.0 grams of 98% methane sulfonic acid in 150 milliliters of water were added with stirring 79.0 grams of octyl dimethyl amine. The temperature of the reaction was maintained at 60°-65° C. The pH of the resulting solution was determined to be 1.5 and was subsequently adjusted to 6 with additional octyl dimethyl amine. The solution was charged to an autoclave, which was pressurized with nitrogen to 30 psig (0.2 MPa). The contents in the autoclave were heated to 70° C. and 48.0 grams of ethylene oxide were added over a period of 30 minutes. Thereafter the reaction mixture was stirred at 70° C. for 1.5 hours. The pressure in the autoclave was released and the reaction product stripped in vacuo to obtain 174.0 grams of a liquid product which remained liquid even on prolonged storage. The product was identified by mass spectroscopy to correspond to the products $C_8H_{17}N$ $(CH_3)_2$ $(CH_2CH_2O)_xH$ $CH_3SO_3$, wherein x was 1, 2 and 3.

EXAMPLE 15

A solution of 68.5 grams of 70% methane sulfonic acid in 150 milliliters of water were neutralized with 107.0 grams of dodecyl dimethyl amine at 80°-90° C. The pH of the neutralized solution was determined to be 1.8, which was subsequently adjusted to 5 with additional dodecyl dimethyl amine. The resulting solution was charged to an autoclave, which was pressurized with nitrogen to 20 psig (0.1 MPa), and the solution heated to 70° C. 68.0 grams of ethylene oxide was added to the autoclave over 45 minutes. After addition of the ethylene oxide, the reactor contents were stirred for one hour while maintaining it at 70° C. Pressure in the autoclave was released and the liquid product stripped in vacuo to obtain 224.0 grams of a liquid product. Mass spectroscopy showed the product to be a mixture of the mono- and diethoxylated quaternary amine, i.e., $C_{12}H_{25}N(CH_3)_2(CH_2CH_2O)_xH$, wherein x is 1 and 2.

Although the present invention has been described with reference to specific details of certain embodiments thereof, it is not intended that such details should be regarded as limitations upon the scope of the invention except as and to the extent that they are included in the accompanying claims.

I claim:

1. A quaternary ammonium compound represented by the graphic formula:

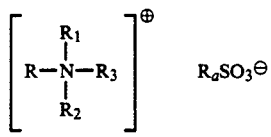

wherein R is octyl, $R_1$ and $R_2$ are each selected form the group consisting of $C_1$-$C_2$ alkyl and the radical, —$CH_2$—$C(A)H$—$O]_xH$, $R_3$ is the radical, —$CH_2$—$C(A)$-$H$—$O]_xH$, $R_a$ is $C_1$-$C_2$ alkyl, A is selected from the consisting of hydrogen, methyl and ethyl, and x is 1.

2. The quaternary ammonium compound of claim 1 wherein $R_1$ and $R_2$ are each methyl, $R_a$ is methyl, and A is hydrogen.

3. The quaternary ammonium compound of claim 1 wherein $R_1$ is methyl, $R_2$ and $R_3$ are each the radical, —$CH_2$—$C(A)H$—$O]_xH$, $R_a$ is methyl and A is hydrogen.

4. The quaternary ammonium compound of claim 1 wherein $R_1$, $R_2$ and $R_3$ are each the radical, —$CH_2$—$C(A)H$—$O]_xH$, $R_a$ is methyl and A is hydrogen.

5. The quaternary ammonium compound represented by the graphic formula:

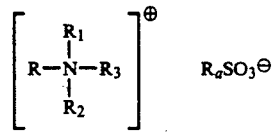

wherein R is selected from the group consisting of soya, cocyl and decyl, $R_1$ and $R_2$ are each selected from the group consisting of $C_1$-$C_2$ alkyl and the radical, [$CH_2$—$C(A)H$—$O]_xH$, $R_3$ is the radical [$CH_2$—$C(A)$-$H$—$O]_xH$, Ra is $C_1$-$C_2$ alkyl, A is selected form the group consisting of hydrogen, methyl and ethyl, and x is 1.

6. The quaternary ammonium compound of claim 5 wherein R is soya, $R_1$ and $R_2$ are each methyl, Ra is methyl and A is hydrogen.

* * * * *

UNITED STATES PATENT AND TRADEMARK OFFICE
CERTIFICATE OF CORRECTION

PATENT NO. : 5,053,531

DATED : Oct. 1, 1991

INVENTOR(S) : Cheruthur Govindan

It is certified that error appears in the above-identified patent and that said Letters Patent is hereby corrected as shown below:

Column 11, claim 1, line 30, "form" should be --from--;

lines 31 and 32, "—$CH_2$—$C(A)H$—$O]_xH$" should be -- $\{CH_2-C(A)H-O]_xH$ --;

line 32 and column 12, line 1, "—$CH_2$—$C(A)H$—$O]_xH$" should be -- $\{CH_2-C(A)H-O]_xH$ --;

Column 12, claim 3, line 8, "—$CH_2$—$C(A)H$—$O]_xH$" should be -- $\{CH_2-C(A)H-O]_xH$ --.

Column 12, claim 4, lines 11 and 13, "—$CH_2$—$C(A)H$—$O]_xH$" should be -- $\{CH_2-C(A)H-O]_xH$ --.

UNITED STATES PATENT AND TRADEMARK OFFICE
CERTIFICATE OF CORRECTION

PATENT NO. : 5,053,531

DATED : October 1, 1991

INVENTOR(S) : Cheruthur Givindan

It is certified that error appears in the above-identified patent and that said Letters Patent is hereby corrected as shown below:

Column 12, claim 5, line 25, "$[CH_2\text{---}C(A)H\text{---}O]_xH$" should be --$\{CH_2\text{-}C(A)H\text{-}O]_xH$ --;

lines 25-26, "$[CH_2\text{---}C(A)H\text{---}O]_xH$" should be --$\{CH_2\text{-}C(A)H\text{-}O]_xH$ --;

line 27, "form" should be --from--.

Signed and Sealed this

Twentieth Day of July, 1993

Attest:

MICHAEL K. KIRK

Attesting Officer

Acting Commissioner of Patents and Trademarks